(12) United States Patent
Shturman

(10) Patent No.: US 9,757,144 B2
(45) Date of Patent: Sep. 12, 2017

(54) ROTATIONAL ATHERECTOMY DEVICE WITH DISTAL EMBOLIC PROTECTION

(71) Applicant: Cardio Flow, Inc., St. Paul, MN (US)

(72) Inventor: Leonid Shturman, Nyon (CH)

(73) Assignee: Cardio Flow, Inc., St. Paul, MN (US)

( * ) Notice: Subject to any disclaimer, the term of this patent is extended or adjusted under 35 U.S.C. 154(b) by 121 days.

(21) Appl. No.: 14/937,546

(22) Filed: Nov. 10, 2015

(65) Prior Publication Data

US 2016/0058468 A1 Mar. 3, 2016

Related U.S. Application Data

(60) Division of application No. 14/189,319, filed on Feb. 25, 2014, now Pat. No. 9,211,138, which is a
(Continued)

(30) Foreign Application Priority Data

Apr. 3, 2009 (GB) .................................... 09057514

(51) Int. Cl.
*A61B 17/3207* (2006.01)
*A61B 17/22* (2006.01)
(Continued)

(52) U.S. Cl.
CPC .. *A61B 17/320758* (2013.01); *A61B 19/5225* (2013.01); *A61B 2017/22067* (2013.01); *A61B 2017/22068* (2013.01); *A61B 2017/22079* (2013.01); *A61B 2017/320766* (2013.01); *A61B 2090/3782* (2016.02)

(58) Field of Classification Search
CPC .... A61B 17/320758; A61B 17/320783; A61B 2017/320766; A61B 2017/22067; A61B 2017/22068; A61B 2017/22079; A61B 2017/22075; A61B 2017/22078;
(Continued)

(56) References Cited

U.S. PATENT DOCUMENTS

| 1,431,416 A | 10/1922 | Parsons et al. |
| 1,916,085 A | 6/1933 | Summers et al. |

(Continued)

FOREIGN PATENT DOCUMENTS

| EP | 0 419 154 | 3/1991 |
| EP | 0 820 729 | 1/1998 |

(Continued)

OTHER PUBLICATIONS

Yolaine Cussac, Authorized Officer, International Bureau of WIPO, International Preliminary Report on Patentability, International Application No. PCT/EP2010/054548, mailed Oct. 13, 2011, 9 pages.

(Continued)

*Primary Examiner* — Jocelin Tanner
(74) *Attorney, Agent, or Firm* — Fish & Richardson P.C.

(57) ABSTRACT

A rotational atherectomy device for removing a stenotic tissue from the iliac artery of a patient. The device comprises a flexible, rotatable drive shaft having an elongated proximal portion, an elongated distal portion, and an abrasive element mounted to the drive shaft between the elongated proximal and distal portions of the drive shaft and configured for rapid rotation together with the drive shaft.

18 Claims, 14 Drawing Sheets

Related U.S. Application Data continuation of application No. 13/262,797, filed as application No. PCT/EP2010/054548 on Apr. 6, 2010, now Pat. No. 8,663,261.

(51) Int. Cl.
 *A61B 90/00* (2016.01)
 *A61B 19/00* (2006.01)

(58) Field of Classification Search
 CPC ........... A61B 2017/22048; A61B 2017/22051; A61B 2017/22069; A61B 2090/3782
 See application file for complete search history.

(56) References Cited

U.S. PATENT DOCUMENTS

| | | | |
|---|---|---|---|
| 4,445,509 A | 5/1984 | Auth | |
| 4,445,892 A | 5/1984 | Hussein et al. | |
| 4,646,736 A | 3/1987 | Auth | |
| 4,870,953 A | 10/1989 | DonMicheal et al. | |
| 4,931,635 A | 6/1990 | Toyama | |
| 4,990,134 A | 2/1991 | Auth et al. | |
| 5,100,425 A | 3/1992 | Fischell et al. | |
| 5,217,474 A | 6/1993 | Zacca et al. | |
| 5,242,460 A | 9/1993 | Klein et al. | |
| 5,250,060 A | 10/1993 | Carbo et al. | |
| 5,273,526 A | 12/1993 | Dance | |
| 5,308,354 A | 5/1994 | Zacca et al. | |
| 5,312,427 A | 5/1994 | Shturman | |
| 5,314,407 A | 5/1994 | Auth et al. | |
| 5,314,438 A | 5/1994 | Shturman | |
| 5,342,292 A | 8/1994 | Nita et al. | |
| 5,361,285 A | 11/1994 | Formanek et al. | |
| 5,370,653 A | 12/1994 | Cragg | |
| 5,458,575 A | 10/1995 | Wang | |
| 5,584,843 A | 12/1996 | Wulfman et al. | |
| 5,681,336 A | 10/1997 | Clement et al. | |
| 5,730,717 A | 3/1998 | Gelbfish | |
| 5,771,895 A | 6/1998 | Slager | |
| 5,843,103 A | 12/1998 | Wulfman | |
| 5,868,708 A | 2/1999 | Hart et al. | |
| 6,010,533 A | 1/2000 | Pope et al. | |
| 6,096,054 A | 8/2000 | Wyzgala et al. | |
| 6,132,444 A | 10/2000 | Shturman et al. | |
| 6,135,982 A | 10/2000 | Campbell | |
| 6,146,395 A | 11/2000 | Kanz et al. | |
| 6,152,911 A | 11/2000 | Giannoble | |
| 6,156,048 A | 12/2000 | Wulfman et al. | |
| 6,241,706 B1 | 6/2001 | Leschinsky et al. | |
| 6,270,465 B1 | 8/2001 | Keith et al. | |
| 6,416,526 B1 | 7/2002 | Wyzgala et al. | |
| 6,485,500 B1 | 11/2002 | Kokish et al. | |
| 6,491,660 B2 | 12/2002 | Guo et al. | |
| 6,565,588 B1 | 5/2003 | Clement et al. | |
| 6,685,718 B1 | 2/2004 | Wyzgala et al. | |
| 6,955,661 B1 | 10/2005 | Herweck et al. | |
| 8,109,954 B2 | 2/2012 | Shturman | |
| 8,109,955 B2 | 2/2012 | Shturman | |
| 8,137,369 B2 | 3/2012 | Shturman | |
| 8,142,458 B2 | 3/2012 | Shturman | |
| 8,147,507 B2 | 4/2012 | Shturman | |
| 8,157,825 B2 | 4/2012 | Shturman | |
| 8,388,636 B2 | 3/2013 | Shturman | |
| 8,388,637 B2 | 3/2013 | Shturman | |
| 8,454,638 B2 | 6/2013 | Shturman | |
| 8,465,510 B2 | 6/2013 | Shturman | |
| 8,496,678 B2 | 7/2013 | Shturman | |
| 8,500,764 B2 | 8/2013 | Shturman | |
| 8,500,765 B2 | 8/2013 | Shturman | |
| 8,663,195 B2 | 3/2014 | Shturman | |
| 8,663,260 B2 | 3/2014 | Shturman | |
| 8,663,261 B2 | 3/2014 | Shturman | |
| 2002/0007190 A1 | 1/2002 | Wulfman et al. | |
| 2002/0082547 A1 | 6/2002 | Deniega et al. | |
| 2002/0099367 A1 | 7/2002 | Guo et al. | |
| 2002/0138088 A1 | 9/2002 | Nash et al. | |
| 2002/0188276 A1 | 12/2002 | Evans et al. | |
| 2003/0199889 A1 | 10/2003 | Kanz et al. | |
| 2004/0098014 A1 | 5/2004 | Flugelman et al. | |
| 2004/0158270 A1 | 8/2004 | Wyzgala et al. | |
| 2005/0154416 A1 | 7/2005 | Herweck et al. | |
| 2005/0209615 A1 | 9/2005 | Prudnikov et al. | |
| 2005/0240146 A1 | 10/2005 | Nash et al. | |
| 2005/0256461 A1 | 11/2005 | DiFiore et al. | |
| 2008/0097498 A1 | 4/2008 | Shimizu et al. | |
| 2008/0319415 A1 | 12/2008 | Shturman | |
| 2009/0018564 A1 | 1/2009 | Shturman | |
| 2009/0069829 A1 | 3/2009 | Shturman | |
| 2009/0182359 A1 | 7/2009 | Shturman | |
| 2009/0312777 A1 | 12/2009 | Shturman | |
| 2009/0318942 A1 | 12/2009 | Shturman | |
| 2009/0326568 A1 | 12/2009 | Shturman | |
| 2010/0010522 A1 | 1/2010 | Shturman | |
| 2010/0049226 A1 | 2/2010 | Shturman | |
| 2011/0054332 A1 | 3/2011 | Shturman | |
| 2012/0035633 A1 | 2/2012 | Shturman et al. | |
| 2012/0109170 A1 | 5/2012 | Shturman | |
| 2012/0191113 A1 | 7/2012 | Shturman | |
| 2013/0178881 A1 | 7/2013 | Shturman | |
| 2013/0245654 A1 | 9/2013 | Shturman | |
| 2013/0274773 A1 | 10/2013 | Shturman | |
| 2013/0296904 A1 | 11/2013 | Shturman | |
| 2013/0296905 A1 | 11/2013 | Shturman | |
| 2013/0310589 A1 | 11/2013 | Shturman | |

FOREIGN PATENT DOCUMENTS

| | | |
|---|---|---|
| EP | 1 820 458 | 8/2007 |
| WO | WO 98/50101 | 11/1998 |
| WO | WO 99/44513 | 9/1999 |
| WO | WO 01/15759 | 3/2001 |
| WO | WO 02/09599 | 2/2002 |
| WO | WO 2006/126076 | 11/2006 |
| WO | WO 2006/126175 | 11/2006 |
| WO | WO 2006/126176 | 11/2006 |
| WO | WO 2008/006704 | 1/2008 |

OTHER PUBLICATIONS

Declaration of Aleksey Filippov, Apr. 23, 2007, 1 page.
Declaration of Dmitri Prudnikov, Apr. 23, 2007, 1 page.
Excerpt from Deposition of Dmitri Prudnikov, Mar. 5, 2008, 7 pages.
Excerpt from Deposition of Dmitri Prudnikov, Mar. 6, 2008, 54 pages.
Exhibits Nos. 14, 31 & 32, from Deposition of Dmitri Prudnikov, Mar. 5, 2008, 3 pages.
Exhibits Nos. 33-39 from Deposition of Dmitri Prudnikov, Mar. 6, 2008, 47 pages.

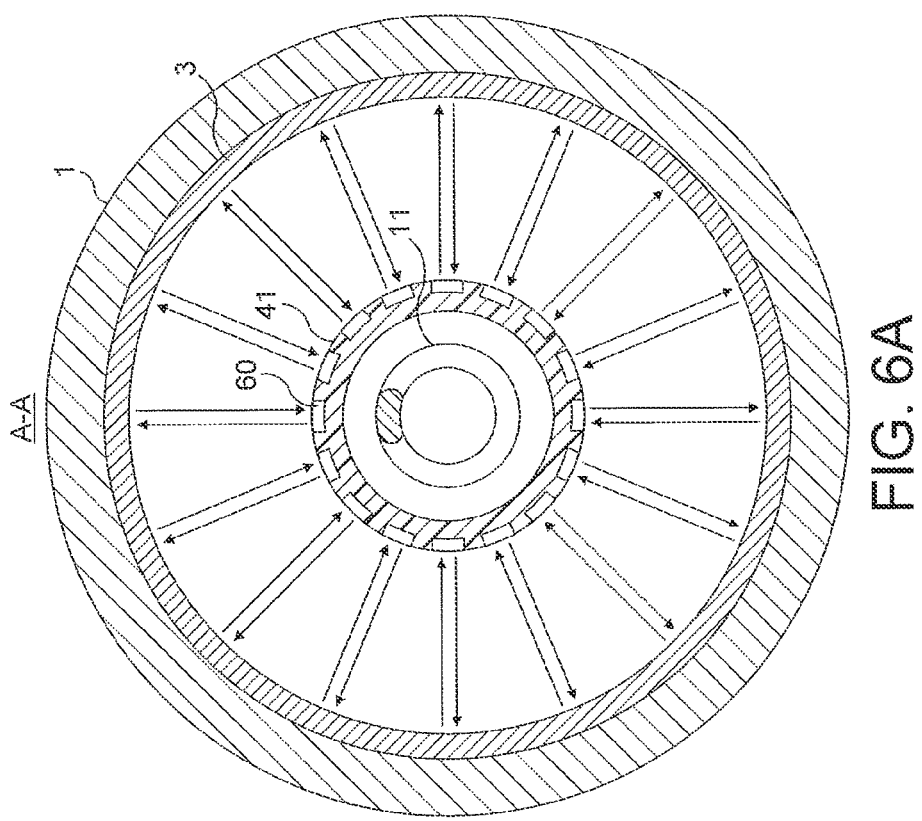

ROTATIONAL ATHERECTOMY DEVICE WITH DISTAL EMBOLIC PROTECTION

CROSS-REFERENCE TO RELATED APPLICATIONS

This application is a divisional of U.S. application Ser. No. 14/189,319 filed Feb. 25, 2014, which is a continuation of U.S. application Ser. No. 13/262,797 filed on Oct. 21, 2011 know U.S. Pat. No. 8,663,261), which is national phase application based on PCT/EP2010/054548 filed on Apr. 6, 2010, which claims priority of GB Patent Application No. 09057514 filed on Apr. 3, 2009, the entire contents of these prior applications being incorporated herein by reference.

DESCRIPTION

The present invention relates to a rotational atherectomy device for removing a stenotic lesion from within a vessel of a patient. More specifically, the invention relates to a rotational atherectomy device for removing or reducing a stenotic lesion in the iliac artery by rotating an abrasive element within the artery to partially or completely ablate the stenotic lesion and simultaneously remove out of the patient's body abraded particles (embolic particles or debris) released into the treated artery during the rotational atherectomy procedure. It should be understood that rotational atherectomy devices and rotational atherectomy procedures are often referred to as rotational angioplasty devices and rotational angioplasty procedures. One type of rotational atherectomy devices is referred to as an orbital atherectomy device. All these terms may be used interchangeably herein.

Atherosclerosis, the clogging of arteries, is a leading cause of coronary heart disease. Blood flow through the peripheral arteries (e.g., carotid, femoral, renal, etc.), is similarly affected by the development of atherosclerotic blockages. One conventional method of removing or reducing blockages in blood vessels is known as rotational atherectomy. A device and a method for performing the Rotational Atherectomy Procedure are known from U.S. Pat. No. 4,990,134 to Auth. A rotational atherectomy (angioplasty) device based on this patent is commercially available from Boston Scientific Corporation of Natik, Mass., USA. The Auth device includes an abrasive burr which is attached to a distal end of a hollow flexible drive shaft. The abrasive surface of the burr is formed from diamond particles. The device is rotated around a special guidewire, which is advanced across the stenotic lesion. The device is advanced towards the stenotic lesion around (over) the guidewire. The abrasive burr is positioned against the occlusion and the drive shaft is rotated around the guidewire at extremely high speeds (e.g., 20,000-160,000 rpm). As the abrasive burr rotates, the physician repeatedly advances it towards the stenotic lesion so that the abrasive surface of the burr scrapes against the occluding tissue and disintegrates it, reducing the occlusion and improving the blood flow through the vessel. It should be understood that the terms abrasive burr and abrasive element may be used interchangeably herein.

U.S. Pat. No. 6,132,444 to Shturman (the instant inventor) et al., describes another rotational atherectomy device of the prior art. The Shturman device comprises an abrasive element located proximal to and spaced away from a distal end of the drive shaft. This abrasive element is formed from diamond particles directly electroplated to wire turns of an enlarged diameter portion of the drive shaft. The enlarged diameter portion of the drive shaft is asymmetric and is responsible for providing an abrasive element with a centre of mass which is spaced away from the rotational axis of the drive shaft. The device is rotated around a special guidewire and its eccentric abrasive element is able to open the treated stenotic lesion to a diameter substantially larger than the maximum diameter of the abrasive element.

U.S. Pat. No. 7,507,245 to Shturman (the instant inventor) et al., describes a third embodiment of the rotational atherectomy device of the prior art. The device of U.S. Pat. No. 7,507,245 is similar to the device of U.S. Pat. No. 6,132,444 except that the abrasive element comprises a prefabricated abrasive crown disposed around the eccentric enlarged diameter portion of the drive shaft. The device is commercially produced by Cardiovascular Systems, Inc. of St. Paul, Minn.

The Patent Application WO 2006/126176 to Shturman (the current inventor) describes a rotational atherectomy device comprising a solid eccentric abrasive element and two solid asymmetric support elements mounted on a hollow flexible drive shaft. The solid asymmetric support elements have their centres of mass spaced away (offset) from a rotational (longitudinal) axis of the drive shaft and, during rotation of the drive shaft, act as counterweights to the eccentric abrasive element. In the most preferred embodiment of the invention, the centre of mass of each of the solid counterweights is separated from the centre of mass of the abrasive element by an angle of 180 degrees around the axis of the drive shaft. When the drive shaft of the rotational atherectomy device with solid counterweights is rotated, centrifugal forces generated by the solid counterweights and the eccentric abrasive element preferably act in substantially the same plane but in opposite directions. These centrifugal forces cause the distal end portion of the drive shaft to flex and assume a generally bowed or arcuate shape. During rotation of the drive shaft, the abrasive element and each of two solid counterweights move in orbital fashions around the axis of rotation of the drive shaft in orbits that are substantially larger than the respective diameters of the abrasive element or solid counterweights.

Disadvantages associated with either limited or completely absent distal embolic protection of all commercially available rotational atherectomy devices have been addressed in WO 2006/126076 to Shturman (the instant inventor). In accordance with WO 2006/126076 drive shaft has a fluid impermeable wall and allows an antegrade flow of pressurised fluid through a lumen of the drive shaft from a proximal end towards a distal end of the drive shaft. A portion of the pressurised fluid, after entering the treated vessel distal to the abrasive element, flows in a retrograde direction around the abrasive element and across the treated stenotic lesion to entrain abraded embolic particles and evacuate them from the treated vessel as soon as they have been abraded by the abrasive element of the device. Several other embodiments of the device with distal embolic protection capability are disclosed in WO 2008/006704, WO 2008/006705, WO 2008/006706, WO 2008/006708, and WO 2008/062069 to Shturman (the instant inventor), but in every one of these embodiments the abraded particles are entrained and evacuated from the patient's body by fluid which flows around the abrasive element in the retrograde direction (i.e. against the direction of the flow of blood in the treated artery).

Over the last few years Edwards Lifesciences Corp. and CoreValve, Inc. (both of Irvine, Calif.) introduced to the market and clinical trials respectfully two types of novel Aortic Heart Valves which are configured for Transcatheter Aortic Valve Replacement. A delivery catheter for transfemoral placement of Edwards SAPIEN Heart Valve has an outer diameter of about 7 millimeters. The Delivery Catheter which is used during the CoreValve ReValving® percutaneous aortic valve replacement procedure has an outer diameter of about 6 millimeters. The delivery catheters of both companies have to be advanced though the Iliac Artery of the patient. A large number of patients who may benefit from the Transcatheter Aortic Valve Replacement have atherosclerotic occlusions in their Iliac Arteries. Often Iliac Arteries of older patients are not only affected by calcified atherosclerotic lesions but are tortuous as well. Therefore what is needed is a rotational atherectomy device which will be able to partially or completely ablate both the soft and calcified stenotic lesions in the tortuous iliac arteries of older patients.

It is the objective of this invention to provide a rotational (orbital) atherectomy device which can ablate atherosclerotic plaques in tortuous iliac arteries and simultaneously remove abraded particles out of the patient's body.

It is another objective of this invention to provide a rotational (orbital) atherectomy device which not only can simultaneously ablate the plaque and remove abraded particles out of the patient, but which can remove abraded particles from the iliac artery without the need to form the retrograde flow of fluid around the abrasive element of the device.

All rotational (orbital) atherectomy devices described above have an abrasive element which is moved back and forth across the stenotic lesion by alternately pulling and pushing on the elongated drive shaft of the device. Pushing on the proximal end of the elongated drive shaft, after removing the guidewire, may cause the flexible drive shaft to bend within the elongated drive shaft sheath. This, in turn, may cause discrepancy between the forward movement of the turbine (the drive shaft is connected to the turbine) and the forward movement of the abrasive element. Therefore, it is yet another objective of this invention to eliminate such a discrepancy by providing a rotational (orbital) atherectomy device in which the abrasive element is moved back and forth across the stenotic lesion by alternately pulling one end of the drive shaft in one direction and the other end of the drive shaft in the opposite direction.

According to a preferred embodiment of the invention, the rotational atherectomy device for removing a stenotic tissue from the iliac artery of a patient is comprising a flexible, rotatable drive shaft having an elongated proximal portion, an elongated distal portion, and an abrasive element mounted to the drive shaft between the elongated proximal and distal portions of the drive shaft and configured for rapid rotation together with the drive shaft, the drive shaft configured for extending throughout an entire length of the iliac artery to be treated and having one elongated portion of the drive shaft extending out of the patient through a first access opening located in a femoral artery which is ipsilateral to the treated artery, and the other elongated portion of the drive shaft extending through a second access opening located in another peripheral artery of the patient.

Preferably, the device includes a pair of elongated drive shaft sheaths, one drive shaft sheath configured for slidably receiving the elongated proximal portion of the drive shaft and the other drive shaft sheath configured for slidably receiving the elongated distal portion of the drive shaft, the drive shaft sheaths having distal ends and being configured for advancement around corresponding portions of the drive shaft into the treated iliac artery such that the distal ends of the sheaths become positioned spaced away from the abrasive element, the space between the distal ends of the drive shaft sheaths allowing to repeatedly move the rotating abrasive element back and forth along the treated iliac artery and abrade the stenotic lesion.

Preferably, one of the drive shaft sheaths should be in a fluid communication with a source of pressurized fluid, said pressurized fluid flows into the treated artery through said one drive shaft sheath, entrains abraded embolic particles, and is drained out from the treated artery through the other drive shaft sheath.

Preferably, an inflatable occlusion balloon should be mounted to at least one of the drive shaft sheaths, the inflatable occlusion balloon being configured, when inflated, to restrict the flow of fluids around the sheath towards and away from the treated stenotic area.

Preferably, an inflatable occlusion balloon is mounted to at least one of the drive shaft sheaths, the inflatable occlusion balloon being mounted near the distal end of the sheath and configured, when inflated, to center the distal end of the drive shaft sheath in the treated artery.

Preferably, an inflatable occlusion balloon should be mounted to each of the two drive shaft sheaths, the inflatable occlusion balloons being mounted near the distal ends of the sheaths and configured, when inflated, to center the distal ends of the drive shaft sheaths in the treated artery.

Preferably, an inflatable occlusion balloon should be mounted to each of the two drive shaft sheaths, the inflatable occlusion balloons being mounted near the distal ends of the sheaths and configured, when inflated, to restrict the flow of fluids around the sheaths towards and away from the treated stenotic area.

Preferably, each of the drive shaft sheaths should be caring an inflatable occlusion balloon, the occlusion balloons being mounted near the distal ends of the sheaths and configured, when inflated, to restrict the flow of fluids around the sheaths towards and away from the treated stenotic area.

Preferably, each of the drive shaft sheaths should be caring an inflatable occlusion balloon, the occlusion balloons being mounted neat the distal ends of the sheaths and configured, when inflated, to center the distal ends on the drive shaft sheaths in the treated artery.

Preferably, at least one of the elongated portions of the drive shaft is configured to be connected to a rotatable shaft of a prime mover, the prime mover being configured for rotating the drive shaft.

Preferably, the prime mover is slidably received within a housing of an advancer mechanism so that an operator can alternately pull and push on the elongated portion of the drive shaft by moving the prime mover back and forth within the housing of the advancer mechanism.

Preferably, the elongated distal portion of the drive shaft is configured to be connected to a rotatable shaft of a prime mover, the prime mover being configured for rotating the drive shaft.

Preferably, the prime mover is slidably received within a housing of an advancer mechanism so that an operator can alternately pull and push on the elongated distal portion of the drive shaft by moving the prime mover back and forth within the housing of the advancer mechanism.

Preferably, the elongated proximal portion of the drive shaft is configured to be connected to a rotatable shaft of a prime mover, the prime mover being configured for rotating the drive shaft.

Preferably, the prime mover is slidably received within a housing of an advancer mechanism so that an operator can alternately pull and push on the elongated proximal portion of the drive shaft by moving the prime mover back and forth within the housing of the advancer mechanism.

Preferably, the device includes a pair of prime movers and each of the elongated portions of the drive shaft is configured to be connected to a rotatable shaft of one of the two prime movers, the prime movers being configured for rotating the drive shaft.

Preferably, each of the prime movers is slidably received within a housing of an advancer mechanism so that an operator can alternately pull on distal and proximal portions of the drive shaft by alternately moving the prime movers away from distal ends of the housings of the advancer mechanisms.

Preferably, proximal ends of both elongated portions of the drive shaft are configured for releasable connection to opposite ends of a rotatable shaft of a prime mover which is configured for rotating the drive shaft.

Preferably, the prime mover is slidably received within a housing of an advancer mechanism so that an operator can alternately pull on distal and proximal portions of the drive shaft by moving the prime mover back and forth within the housing of the advancer mechanism.

Preferably, the device includes a prime mover for rotating the drive shaft and an advancer mechanism which is configured for slidably carrying the prime mover.

Preferably, one of the elongated portions of the drive shaft is configured to be connected to a rotatable shaft of the prime mover, and the drive shaft sheath extending around said portion of the shaft is configured to be connected to a housing of the advancer mechanism so that an operator can repeatedly move the abrasive element back and forth across the stenotic lesion by moving the prime mover back and forth with respect to the housing of the advancer mechanism.

Preferably, the atherectomy device comprises a pair of advancer mechanisms, a first advancer mechanism having a first housing which slidably carries a prime mover configured for rotating the drive shaft, and a second advancer mechanism having a second housing which slidably carries a hollow body comprising a rotatable shaft supported by at least one bearing which is disposed within the hollow body, and one of the two elongated portions of the drive shaft is configured to be connected to a rotatable shaft of the prime mover, and the other of the two elongated portions of the drive shaft being configured to be connected to the rotatable drive shaft of the second advancer mechanism, and the drive shaft sheaths are configured to be connected to distal ends of the housings of the advancer mechanisms so that an operator can move the abrasive element across the stenotic lesion by alternately moving the prime mover and the hollow body away from the distal ends of the housings of the first and second advancer mechanisms.

Preferably, the device comprising a flexible, rotatable drive shaft having an elongated proximal portion, an elongated distal portion, and an abrasive element mounted to the drive shaft between the elongated proximal and distal portions of the drive shaft and configured for rapid rotation together with the drive shaft, the drive shaft configured for extending throughout an entire length of the artery to be treated and having one elongated portion of the drive shaft extending out of the patient through a first access opening located in a femoral artery, and the other elongated portion of the drive shaft extending through a second access opening located in another peripheral artery of the patient.

Preferably, the device includes a pair of elongated drive shaft sheaths, one drive shaft sheath configured for slidably receiving the elongated proximal portion of the drive shaft and the other drive shaft sheath configured for slidably receiving the elongated distal portion of the drive shaft, the drive shaft sheaths having distal ends and being configured for advancement around corresponding portions of the drive shaft into the treated artery such that the distal ends or the sheaths become positioned spaced away from the abrasive element, the space between the distal ends of the drive shaft sheaths allowing to repeatedly move the rotating abrasive element back and forth along the treated artery and abrade the stenotic lesion.

Preferably, one of the drive shaft sheaths is in a fluid communication with a source of pressurized fluid, said pressurized fluid flows into the treated artery through said one drive shaft sheath, entrains abraded embolic particles, and is drained out from the treated artery through the other drive shaft sheath.

Preferably, the device includes a prime mover for rotating the drive shaft.

Preferably, the prime mover is slidably received within a housing of an advancer mechanism so that an operator can repeatedly move the abrasive element back and forth across the stenotic lesion by repeatedly moving the prime mover back and forth within the housing of the advancer mechanism.

Preferably, the device includes an advancer mechanism which is configured for repeatedly moving the rotating prime mover together with the rotating drive shaft and the abrasive element back and forth across the treated stenotic lesion.

Preferably, the elongated drive shaft sheath which is selected for draining fluid out of the treated artery should include a separate drainage lumen which is configured exclusively for draining fluid and abraded particles out from the treated artery.

Preferably, the elongated drive shaft sheaths should include occlusion balloon inflation lumens.

Preferably, the abrasive element has a centre of mass which is spaces away from the longitudinal axis of the drive shaft.

Preferably, each of the two elongated portions of the drive shaft is at least 15 centimeters long.

Preferably, each of the two elongated portions of the drive shaft is at least 30 centimeters long.

Preferably, an ultrasound transducer should be mounted near the distal end of one of the drive shaft sheaths, the ultrasound transducer allowing acquisition of transverse ultrasound images of the treated artery.

Preferably, the second access opening should be located in a femoral artery which is contralateral with respect to the iliac artery to be treated.

Alternatively, the second access opening is located in an artery of the upper extremity of the patient.

The second access opening may be located in one of the radial arteries of the patient.

BRIEF DESCRIPTION OF DRAWINGS

FIG. 1 shows that an eccentric abrasive element is mounted to the drive shaft between a pair of elongated portions of the drive shaft. FIG. 1 shows that one elongated portion of the drive shaft (i.e. distal) extends out of the patient through a first access opening located in the ipsilateral to the lesion femoral artery of the patient and the other elongated portion of the drive shaft (i.e. proximal) extends out of the patient through a second access opening located in the contralateral to the lesion femoral artery of the patient;

FIG. 2 shows that distal ends of the sheaths are spaced away from the abrasive element. FIG. 2 shows occlusion balloons which are mounted to the sheaths near their distal ends. FIG. 2 shows that the elongated portion of the drive shaft on one side of the abrasive element (i.e. ipsilateral) has been connected to a turbine, and the corresponding elongated drive shaft sheath has been connected to an advancer mechanism. The advancer mechanism slidably receives the turbine and allows moving the rotating abrasive element back and forth across the stenotic lesion to be treated;

FIG. 3 illustrates that pressurized fluid flows towards the treated iliac artery through the proximal drive shaft sheath and is drained from the artery through the distal drive shaft sheath. FIG. 3 illustrates that rotation of the drive shaft and its eccentric abrasive element has been initiated and that abraded parades are removed from the patient as soon as they are produced.

FIGS. 4 and 5 show that the inflated occlusion balloons not only restrict the flow of blood towards and away from the treated stenotic lesion but allow centering of the drive shaft within the treated artery as well;

FIG. 6A is a cross-sectional view taken alone the line A-A shown in FIG. 6 and shows an ultrasound image acquired by the ultrasound transducers;

Reference is made in this specification to the "distal" and "proximal" ends of the elongated drive shaft sheaths. For the purpose of this specification, the distal end is considered to refer to the end of the sheath which is located inside the patient's body, and the proximal end is considered to refer to that end of the sheath which is located outside the patient's body. Embolic particles are indicated by symbol "EP", and the flow of fluid through the device is indicated by arrows "F". It should be noted that the terms "guidewire" and "guide wire" are used interchangeably in the medical device literature. The terms "prime mover" and "gas turbine" are used interchangeably throughout this specification as well. It should be understood that any connection of the elongated portion of the drive shaft to a shaft of the prime mover can be made a releasable connection. It should be also understood that any connection of the drive shaft sheath to a housing of an advancer mechanism can be made a releasable connection.

Operation of the rotational atherectomy device to abrade the stenotic lesion located in the iliac artery will now be described with reference to FIGS. 1 to 13 of the accompanying drawings.

Figure 1:
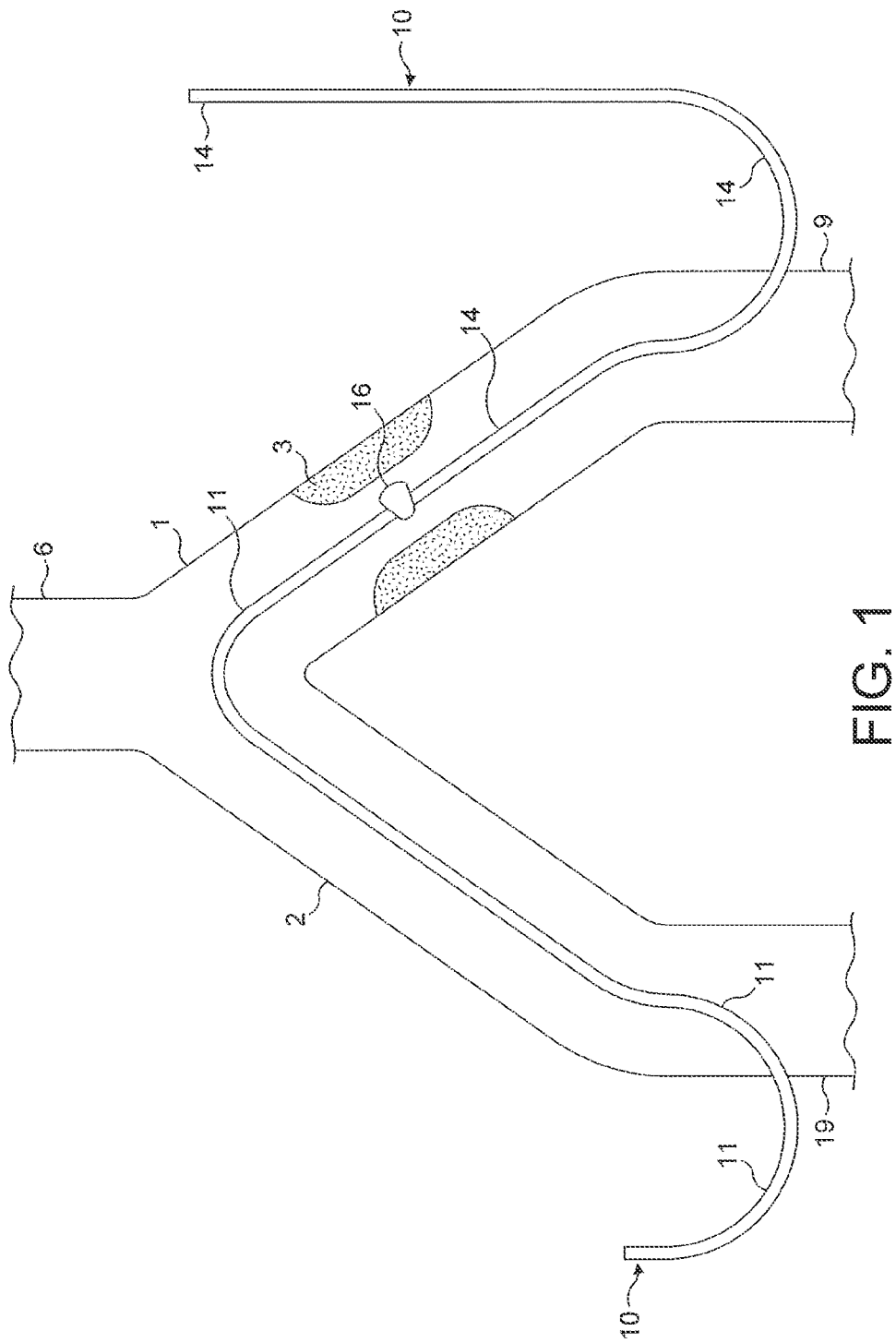
FIG. 1 is a side sectional view of iliac arteries. A stenotic lesion to be treated is located in the right iliac artery. A drive shaft of an atherectomy device of the invention is extending through the iliac arteries.

FIG. 1 is a side sectional view of iliac arteries. A stenotic lesion 3 to be treated is located in the right iliac artery 1. A drive shaft 10 of an atherectomy device of the invention is extending through the iliac arteries. FIG. 1 shows that an eccentric abrasive element 16 is mounted to the drive shaft 10 between a pair of elongated portions of the drive shaft 11, 14. FIG. 1 shows that one elongated portion of the drive shaft (i.e. distal) 14 extends out of the patient through a first access opening located in the ipsilateral to the lesion femoral artery 9 of the patient and the other elongated portion of the drive shaft (i.e. proximal) extends out of the patient through a second access opening located in the contralateral to the lesion femoral artery 19 of the patient. It should be understood that one of the of elongated portions of the drive shaft 11, 14 may be shorter than the other, but even the shorter elongated portion of the drive shaft should have at least 15 centimeters in its length. Preferably, each elongated portion of the drive shaft should have at least 30 centimeters in its length.

It should be noted that the drive shaft 10 may be advanced into its position over the guidewire (not shown). The guidewire may be introduced, for example, from the contralateral side through a percutaneous puncture, and advanced superiorly towards the aorta 6. A retrieval catheter (not shown) is introduced through a vascular access site in the ipsilateral femoral artery and advanced into the ipsilateral iliac artery. The retrieval catheter is used to grasp the guidewire and retract it interiorly through the ipsilateral vascular access site. The above described technique of advancing the guidewire is well known to the interventional cardiologists and interventional radiologists. The guidewire is removed after the drive shaft 10 has been advanced over it.

Figure 2:
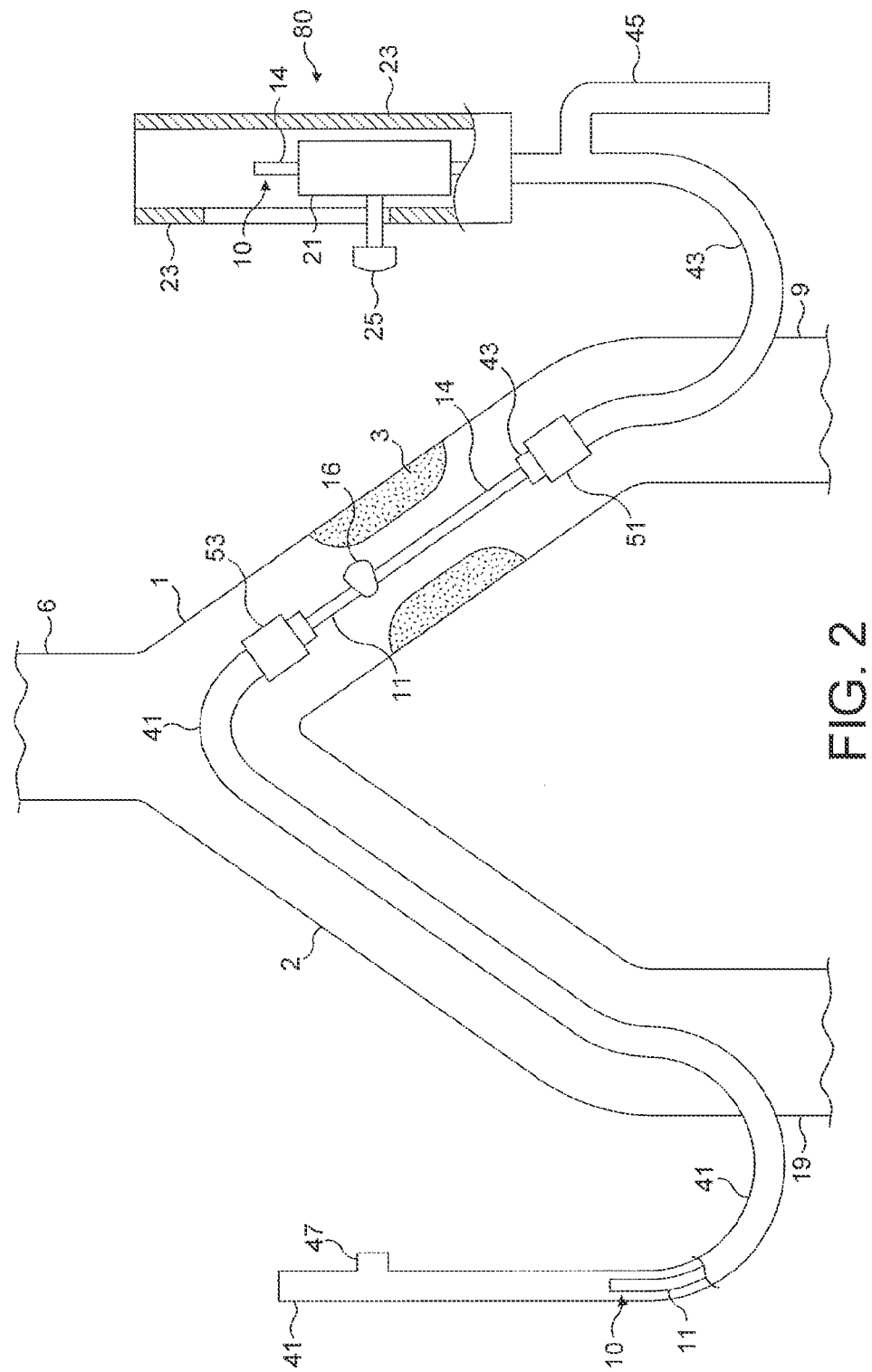
FIG. 2 is a side sectional view which shows that one elongated drive shaft sheath has been advanced over the elongate proximal portion of the drive shaft, and another elongated drive shaft sheath has been advanced over the elongate distal portion of the drive shaft.

FIG. 2 is a side sectional view which shows that one elongated drive shaft sheath 41 has been advanced over the elongate proximal portion 11 of the drive shaft 10, and another elongated drive shaft sheath 43 has been advanced over the elongate distal portion 14 of the drive shaft 10. The elongated drive shaft sheaths 41, 43 are configured for slidably receiving corresponding portions of the drive shaft 10. FIG. 2 shows that the distal ends of the sheaths 41, 43 are spaced away from the abrasive element 16. The space between the distal ends of the elongated sheaths 41, 43 allows moving the rotating abrasive element 16 back and forth along the treated stenotic lesion 3 in the iliac artery 1. FIG. 2 shows that the elongated distal portion 14 of the drive shaft 10 has been connected to a prime mover 21 and the corresponding elongated drive shaft sheath 43 has been connected to a housing 23 of an advancer mechanism 80 which carries the prime mover (i.e. gas turbine) 21. The prime mover 21 is configured for rotating the drive shaft 10. The advancer mechanism 80 slidably receives the prime mover 21 within its housing 23 and allows moving the rotating drive shaft 10 and its abrasive element back and forth across the stenotic lesion to be treated. It should be noted that the prime mover 21 usually includes a gas turbine, but it may be comprised from an electric motor as well. FIG. 2 shows that the proximal drive shaft sheath 41 has a female portion of the Luer Connector 47 near its proximal end. The Luer Connector 47 is configured for connecting the proximal drive shaft sheath 41 to a source of pressurized fluid.

Figure 3:
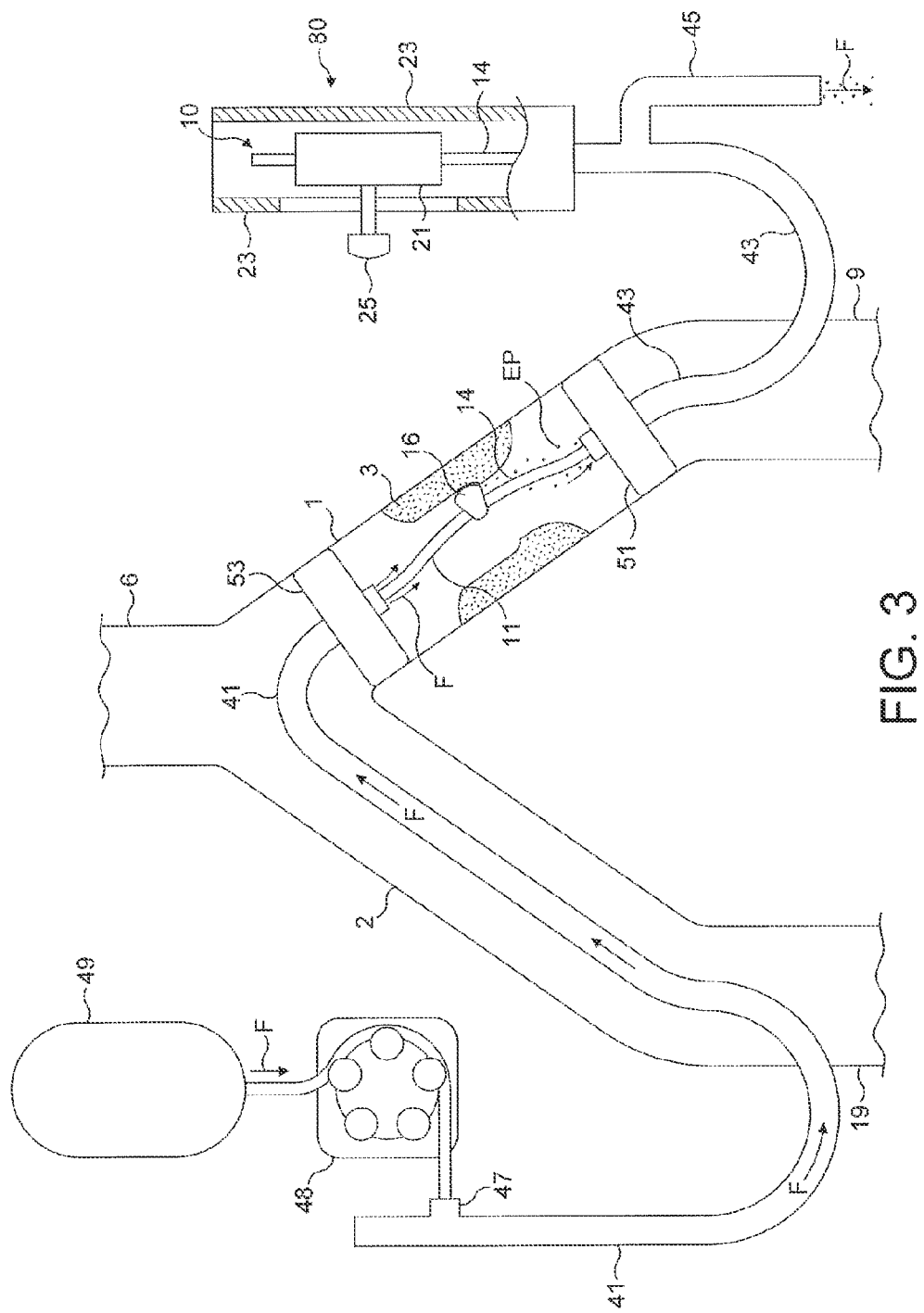
FIG. 3 is a side sectional view which shows that the elongated proximal drive shaft sheath (i.e. on the contralateral side) has been connected to a source of pressurized fluid.

FIG. 3 is a side sectional view which shows that the elongated proximal drive shaft sheath 41 has been connected to a source of pressurized fluid. FIG. 3 illustrates that pressurized fluid flows towards the treated iliac artery 1 through the proximal drive shaft sheath 41 and is drained from the artery through the elongated distal drive shaft sheath 43 and its side branch 45. The direction of the flow of pressurized fluid is indicated by arrows "F". FIG. 3 illustrates that the elongated proximal drive shaft sheath 41 is connected to a bag 49 with the saline solution via a roller pump 48. It should be noted that a power injector or any other suitable pump may be used for pumping fluid into the elongated proximal drive shaft sheath 41. FIG. 3 illustrates that occlusion balloons 51, 53 have been inflated within the treated vessel 1. The occlusion balloons 51, 53 are mounted to the elongated drive shaft sheath 41, 43 near the distal ends of the sheaths. The occlusion balloons 51 and 53, when inflated, not only restrict the flow of blood towards and away from the treated stenotic lesion 3 but allow centering of the drive shaft within the treated artery 1 as well. FIG. 3 shows that rotation of the eccentric abrasive element 16 has been initiated, and centrifugal force caused bowing of that portion of the drive shaft 10 which extends between the distal ends of the elongated drive shaft sheaths 41, 43. It show be noted that the rotating drive shaft is centered along a longitudinal axis of the iliac artery 1 at the distal ends of the sheaths 41, 43 by inflated occlusion balloons 51, 53. The abrasive element 16 is orbiting within the stenotic lesion and abrading it. The weight of the abrasive element 16, its eccentricity, and rotational speed of the turbine define the centrifugal force which is bending the drive shaft and presses the abrasive element 16 against the stenotic tissue 3. It should be noted the potential diameter of the orbit of the eccentric abrasive element become increased when the distance between the distal ends of sheaths is enlarged. FIG. 3 illustrates that abraded particles "EP" are entrained by the flow of fluid and they are removed from the treated iliac artery 1 and the patient's body as soon as they are produced.

Figure 4:
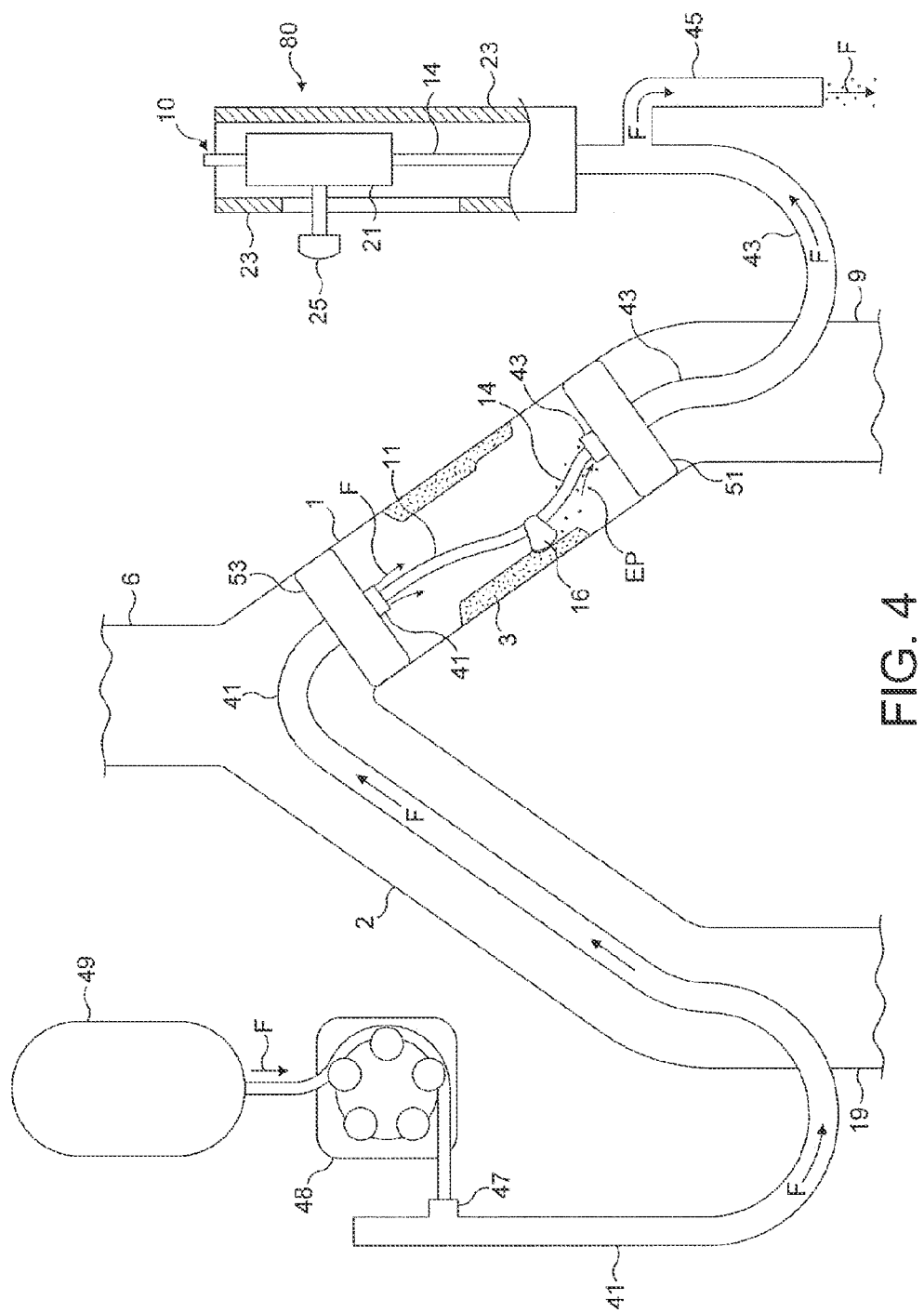
FIGS. 4 and 5 are side sectional views illustrating the process of ablation of the atherosclerotic plaque by the rotating abrasive element which is repetitively moved back and forth across the stenotic lesion.
Figure 5:
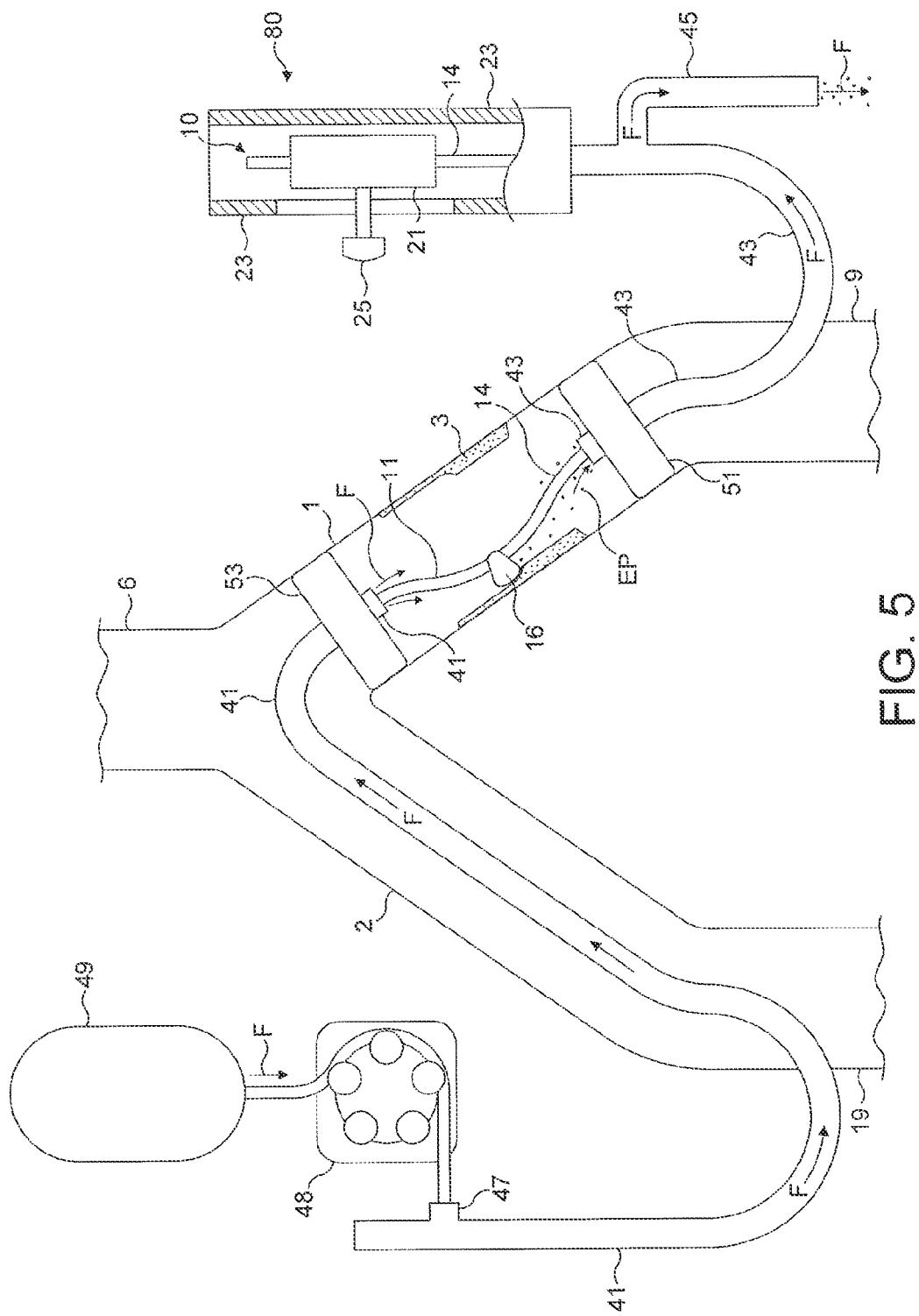

FIGS. 4 and 5 illustrated back and forth movements of the rotating abrasive element along the treated iliac artery 1 and across the stenotic lesion 3. A physician can repeatedly move the rotating abrasive element back and forth by repeatedly moving back and forth the turbine 21 (knob 25) within the housing 23 of the advancer mechanism 80.

Figure 6:
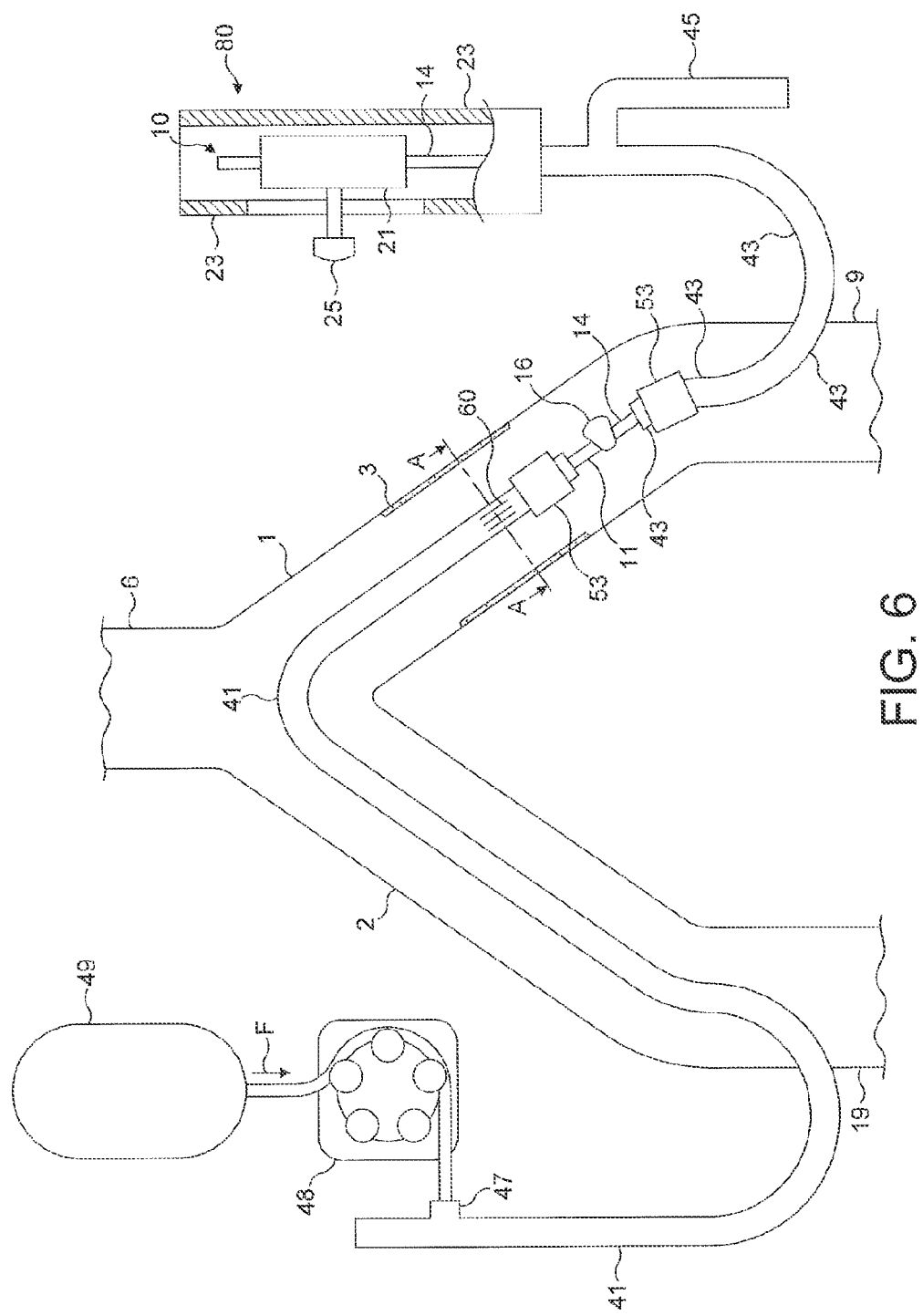
FIG. 6 is a side sectional view illustrating that a plurality of ultrasound transducers can be mounted to a distal end portion of one of the elongated drive shaft sheaths. These transducers allow repeatedly acquiring cross-sectional ultrasound image(s) or the treated vessel throughout the atherectomy procedure and enhancing its safety.

FIG. 6 illustrates that a plurality of ultrasound transducers 60 can be mounted to a distal end portion of the elongated proximal drive shaft sheath 41. These transducers 60 allow repeatedly acquiring cross-sectional ultrasound image(s) of the treated vessel throughout the atherectomy procedure and enhancing its safety. FIG. 6A is a cross-sectional view taken along the line A-A shown in FIG. 6 and shows an ultrasound image acquired by the ultrasound transducers 60.

Figure 7:
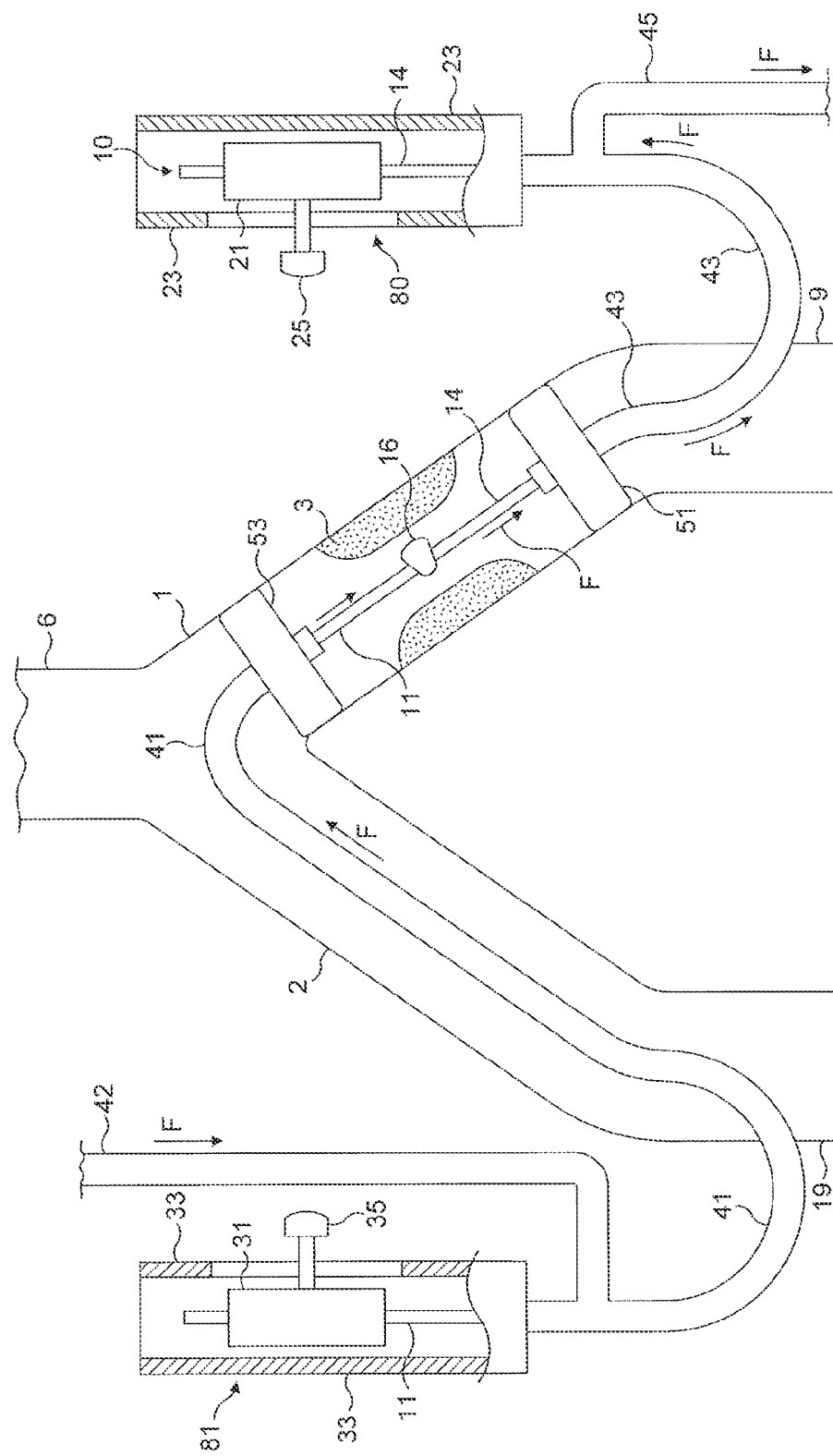
FIGS. 7 through 9 are side sectional views showing that the elongated portion on the drive shaft on each side of the abrasive element can be connected to the advancer mechanism. This allows moving the abrasive element in one direction across the stenotic lesion by pulling on the elongated portion of the drive shaft located on one side of the abrasive element, and moving the abrasive element in the opposite direction by pulling on the elongated portion of the drive shaft located on the other side of the abrasive element.
Figure 8:
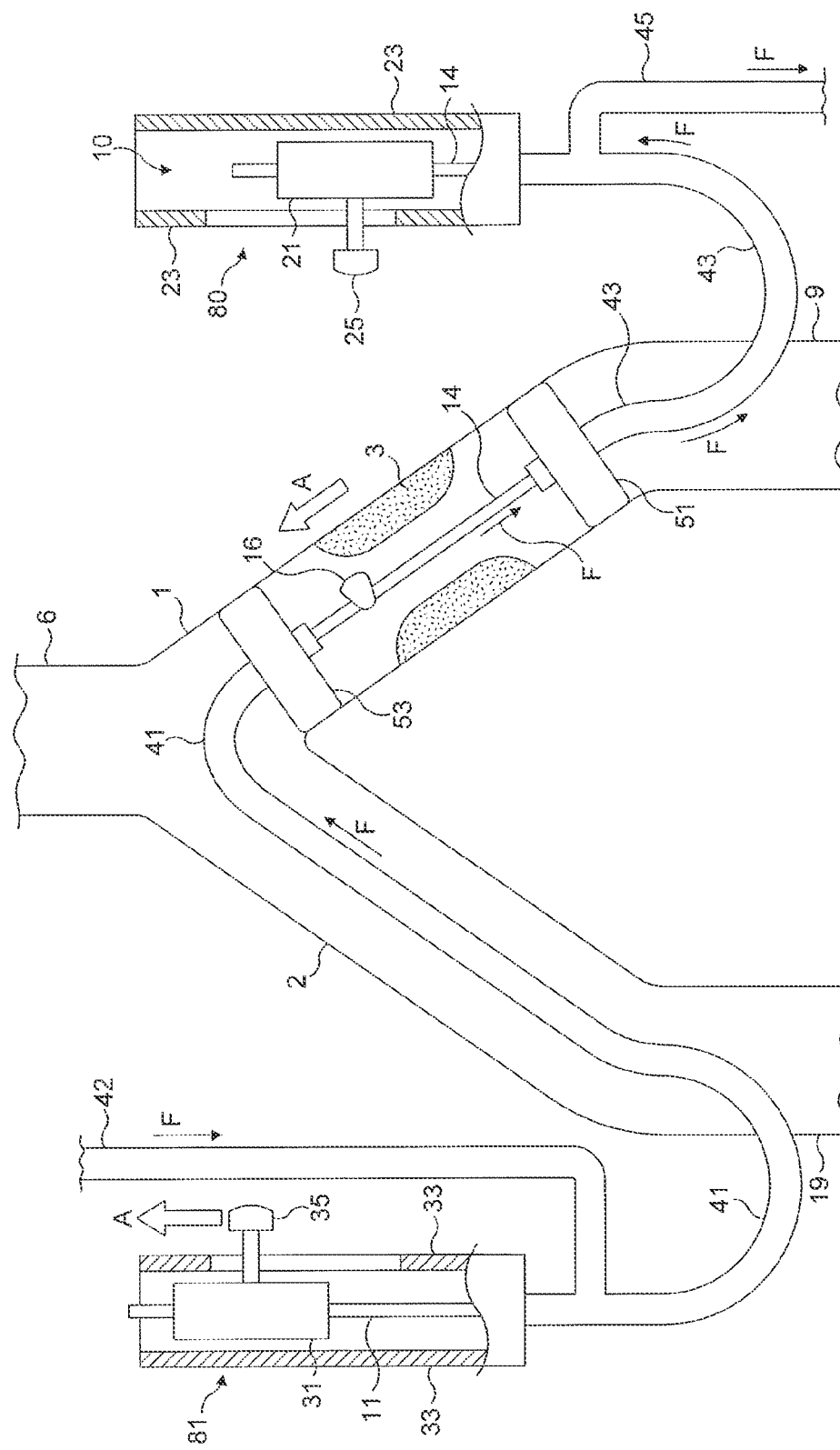
Figure 9:
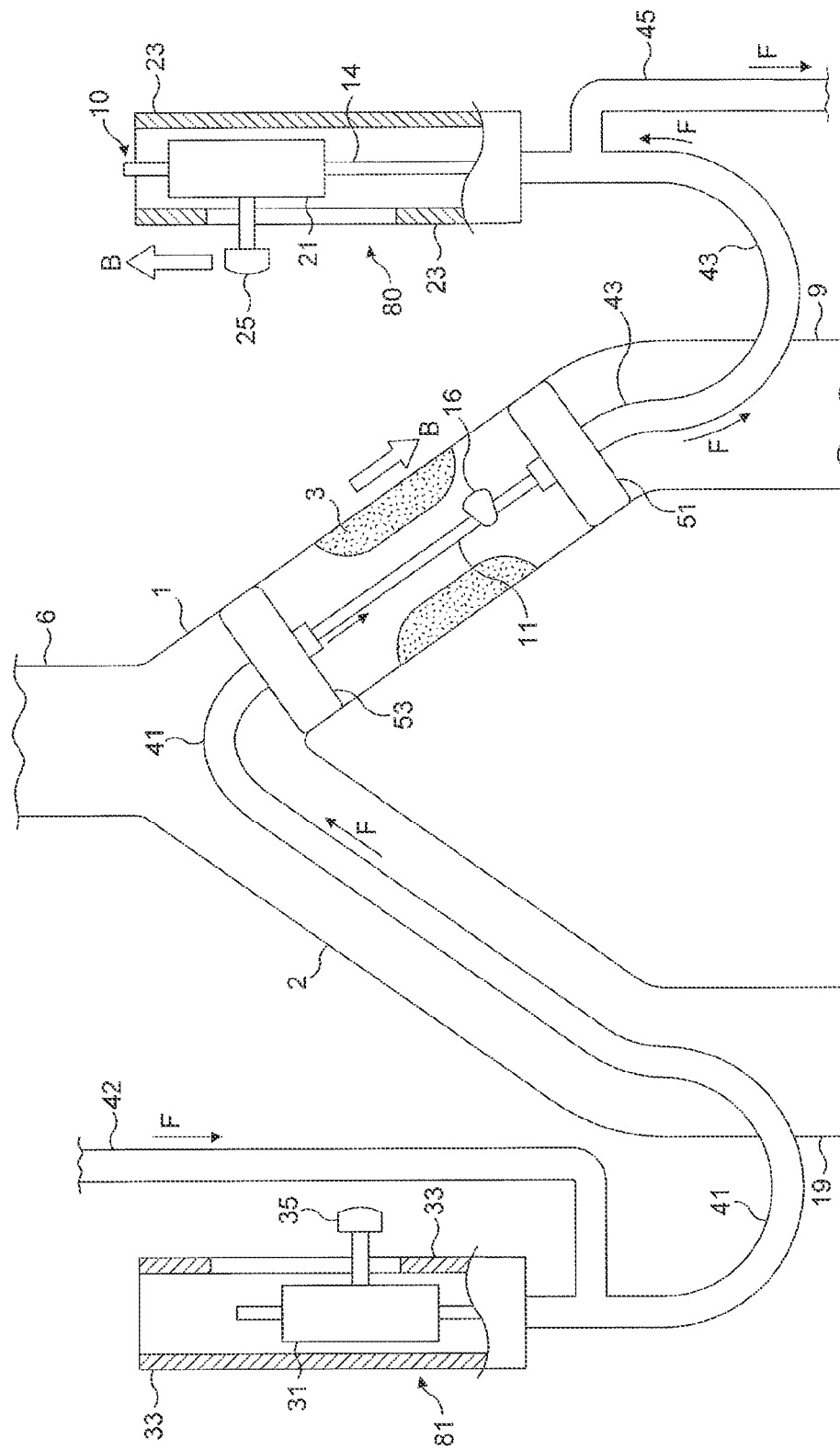

FIGS. 4 and 5 described above illustrated that repeated back and forth movements of the rotating abrasive element 16 along the treated iliac artery 1 and across the stenotic lesion 3 can be achieved by repeatedly moving back and forth the turbine 21 within the housing 23 of the advancer mechanism 80. It should be noted that the back moving turbine 21 pulls the elongated distal portion 14 of shaft 10, and the forward moving turbine 21 pushes on the proximal end of the elongated distal portion 14 of shaft 10. As it was already described, in the preferred embodiment of the invention, the guidewire is used only to advance the drive shaft 10 through the iliac arteries. Pushing on the proximal end of the elongated drive shaft, after removing the guidewire, may cause the flexible drive shaft to bend within the elongated drive shaft sheath 43. This, in turn, may cause discrepancy between the forward movement of the turbine 21 and the forward (proximal) movement of the abrasive element 16. An embodiment shown in FIGS. 7 through 9 is addressing this issue by providing a second advancer mechanisms 81 and moving the abrasive element 16 proximally across the treated stenotic lesion 3 by pulling the elongated proximal portion 11 of the drive shaft 10 by the second turbine 31 instead of pushing on the proximal end of the elongated distal portion 14 of the drive shaft 10 by the turbine 21. The physician is moving the abrasive element 16 in one direction across the stenotic lesion 3 by pulling the proximal end of the elongated portion of the drive shaft located on one side of the abrasive element 16, and the physician is moving the abrasive element 16 in the opposite direction by pulling on the elongated portion of the drive shaft located on the other side of the abrasive element 16. It should be noted that the second advancer mechanism 81 does not need to have a complete turbine assembly and the housing 31 may include only one or two bearings for rotatably supporting the proximal end of the shaft 10.

Figure 10:
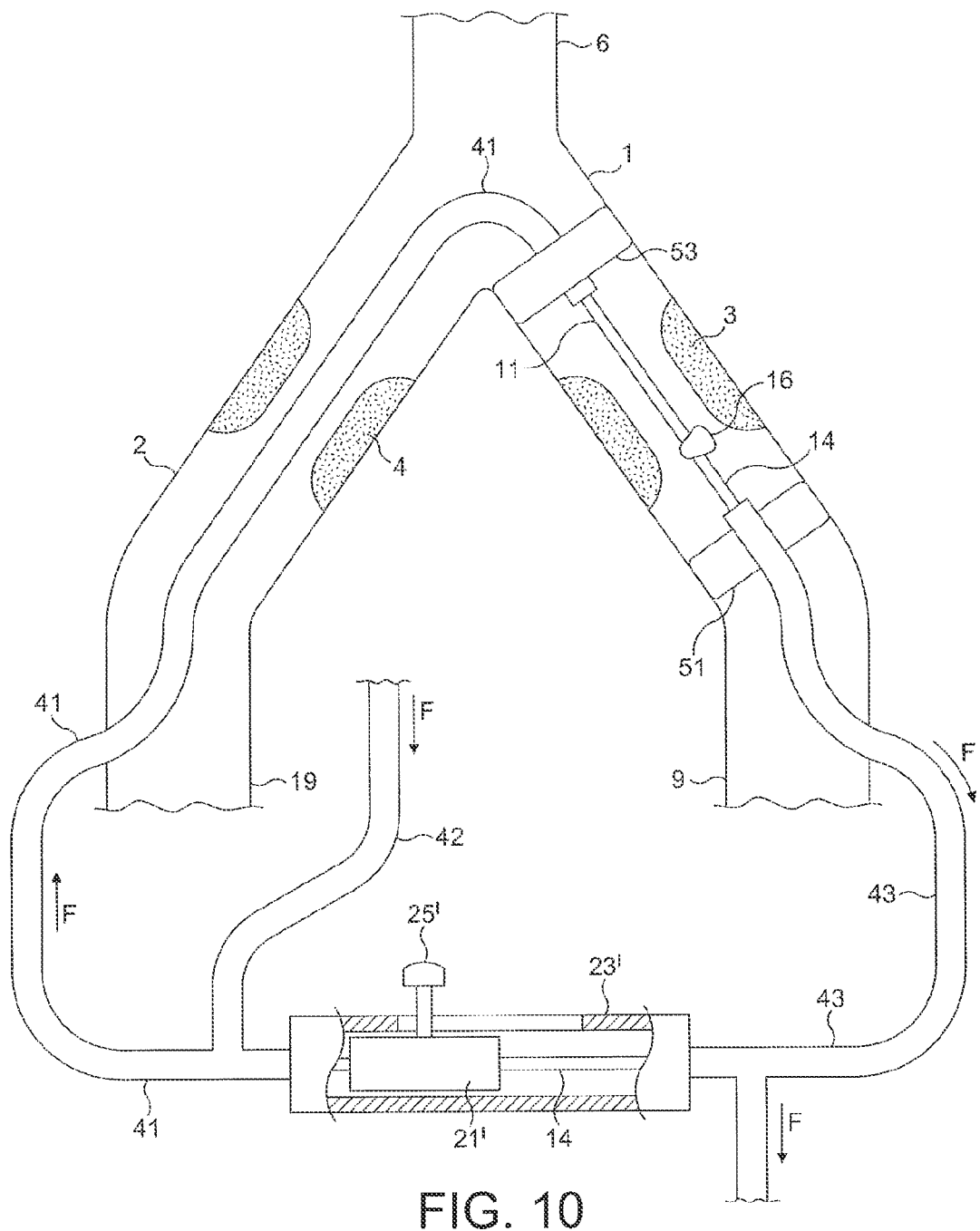
FIGS. 10 and 11 are side sectional views showing that proximal ends of the elongated portions of the drive shaft located on both sides of the abrasive element can be connected to the opposite ends of the same turbine shaft. This allows moving the abrasive element back and forth across the stenotic lesion by simultaneously pulling on one elongated portion of the drive shaft and pushing on the other.
Figure 11:
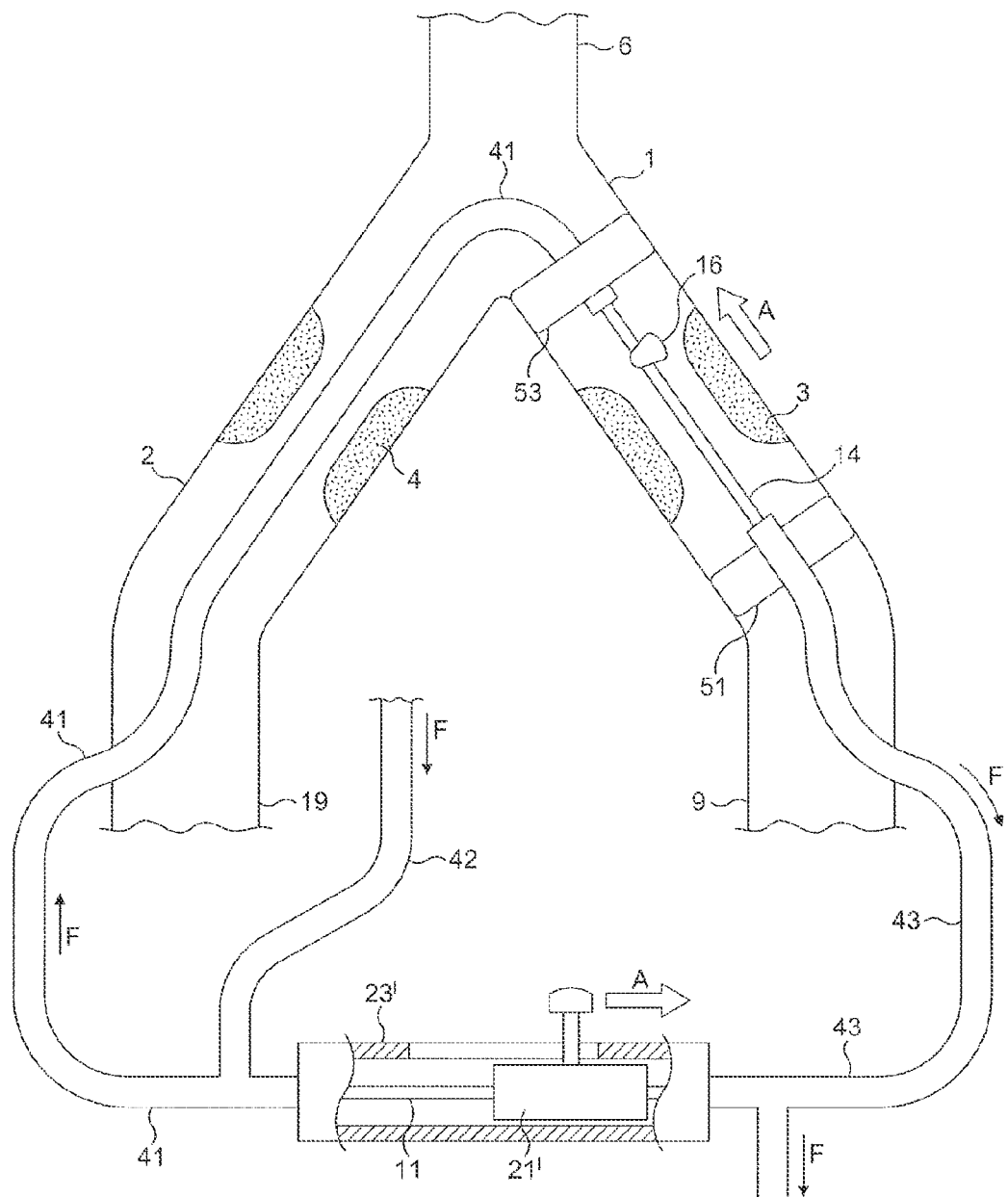

FIGS. 10 and 11 are side sectional views showing that proximal ends of the elongated distal and proximal portions and of the drive shaft 10 (i.e. elongated portions located on the opposite sides of the abrasive element 16) can be connected to the opposite ends of the shaft of the single turbine 23'. This allows moving the abrasive element 16 back and forth across the stenotic lesion 3 by simultaneously pulling on one elongated portion of the drive shaft and pushing on the other. The open arrows "A" in FIG. 11 indicate the direction of movement of the turbine 23' end the abrasive element 16. The turbine 23' in FIG. 11 is pulling the elongated proximal portion 11 of the drive shaft 10 and simultaneously pushing on the elongated distal portion 14 of the drive shaft 10.

Figure 12:
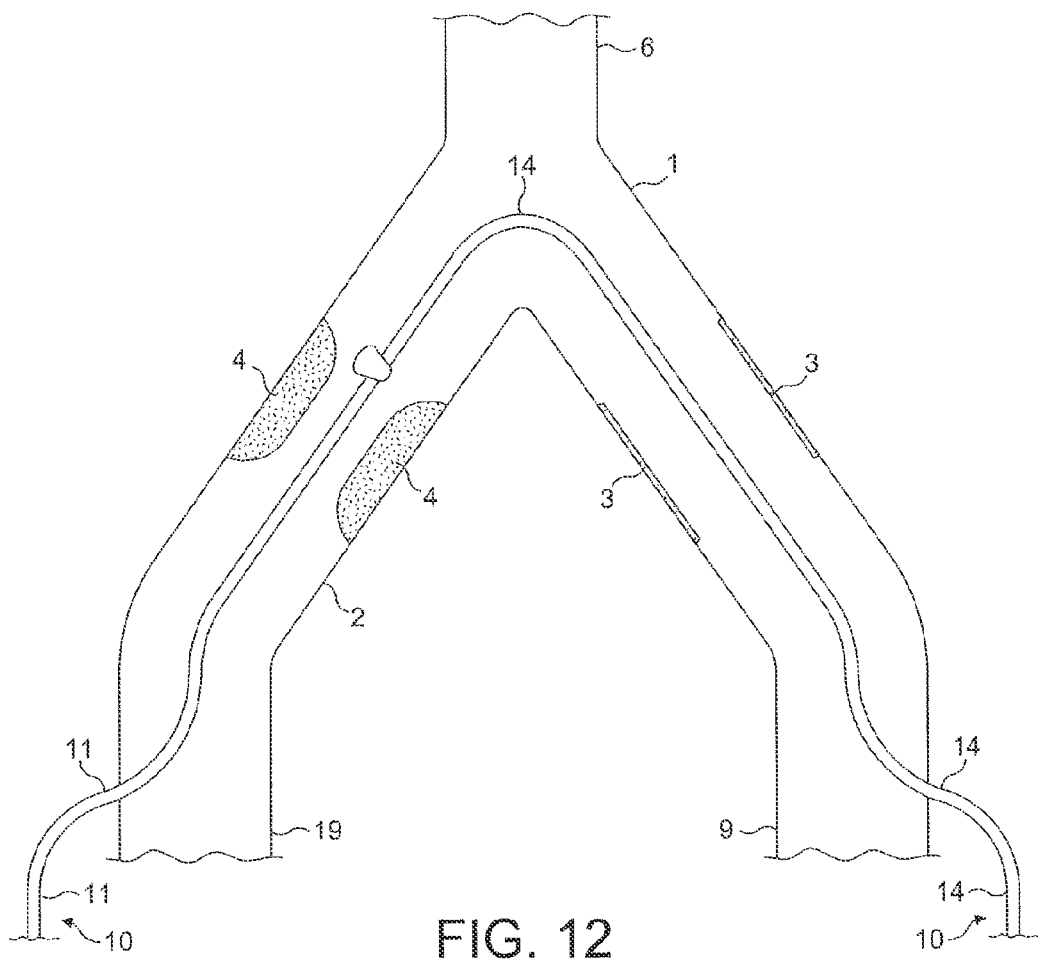
FIG. 12 is a side sectional view illustrating that after completing the treatment of one iliac artery the abrasive element can be repositioned into another iliac artery without removing the drive shaft out of the patient's body.

FIG. 12 is a side sectional view illustrating that after completing the treatment of one iliac artery (i.e. right) the abrasive element 16 can be repositioned into another iliac artery (i.e. left) without removing the drive shaft 10 out of the patient's body.

Figure 13:
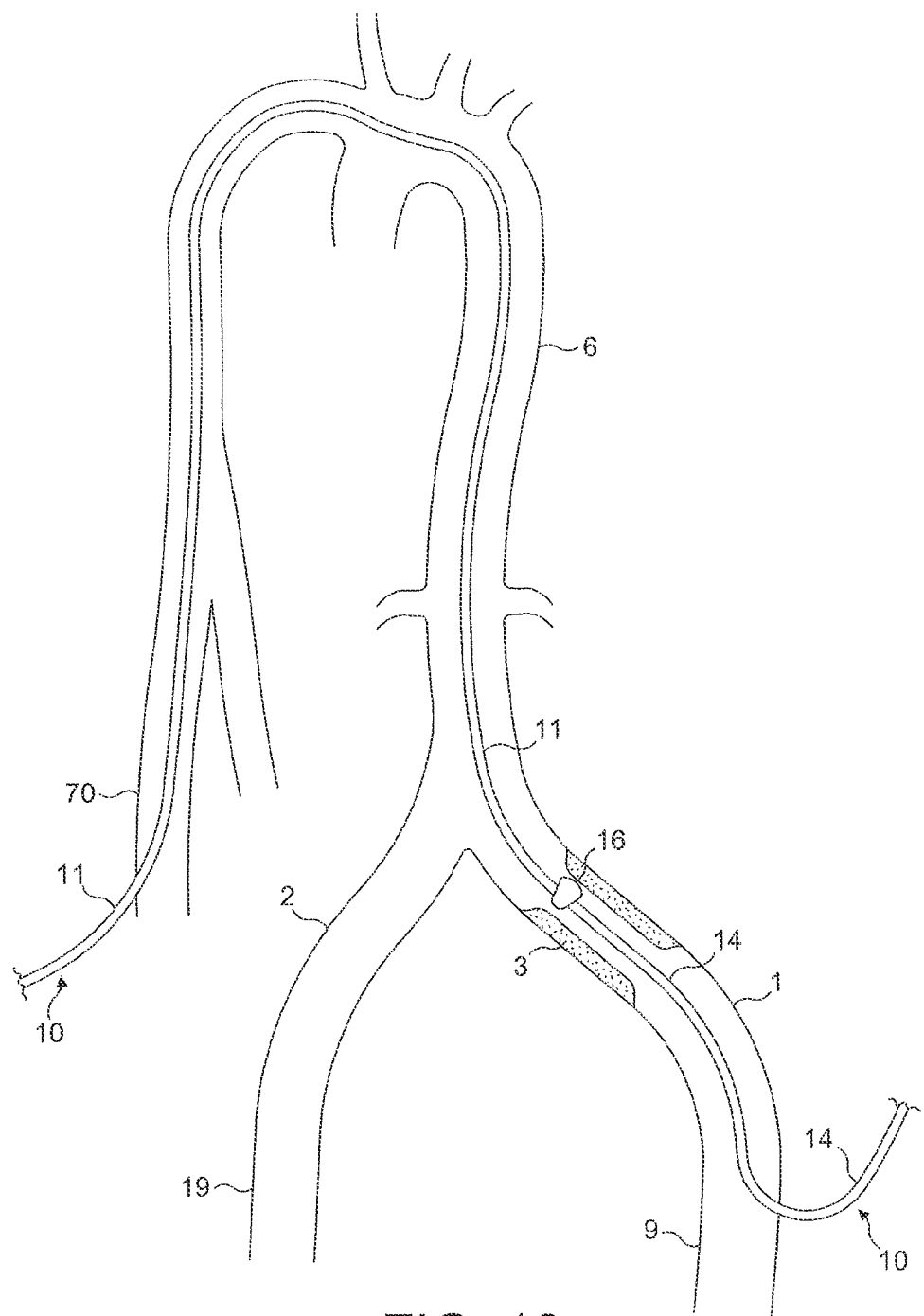
FIG. 13 is a side sectional view illustrating that one elongated portion of the drive shaft (i.e. distal) extends out of the patient through a first access opening located in the ipsilateral to the lesion femoral artery of the patient and the other elongated portion of the drive shaft (i.e. proximal) extends out of the patient through a second access opening located in the radial artery of the patient.

FIG. 13 is a side sectional view illustrating chat one elongated portion of the drive shaft (i.e. distal portion 14) may extend out of the patient through a first access opening located in the ipsilateral femoral artery 9 of the patient and the other elongated portion of the drive shaft (i.e. proximal portion 11) may extend out of the patient through a second access opening located in the radial artery 70 of the patient instead of extending through the access opening in the contralateral femoral artery 19.

It should be noted that radio opaque markers (rings) may be mounted to the drive shaft sheaths in order to facilitate appropriate positioning of the sheaths within the treated iliac artery.

A preferred method of using the rotational (orbital) atherectomy device of the invention for treating a stenotic lesion in the iliac artery should include the following steps:

a) positioning the drive shaft in the iliac arteries such that one elongated portion of the drive shaft extends out of the patient through a first access opening located in the femoral artery winch is ipsilateral to the iliac artery to be treated, and the other elongated portion of the drive shaft extends through a second access opening located in the femoral artery which is contralateral to the iliac artery to be treated;

b) positioning the abrasive element within the stenotic lesion to be treated and locating the drive shaft sheaths in the treated iliac artery such that their distal ends are spaced away from the abrasive element;

c) inflating occlusion balloons of the distal sheaths;

d) initiating the flow of pressurized fluid through the first sheath and draining it through the second sheath; and e) initiating rotation of the drive shaft and repeatedly moving the rotating abrasive element back and forth across the treated stenotic lesion;

f) deflating occlusion balloons, repositioning the abrasive element and the drive shaft sheaths along the treated artery, and repeating the steps b, c, d and e; and g) if the other iliac artery also has a stenotic lesion, then repositioning the abrasive element in the other iliac artery, positioning the drive shaft sheaths in the treated artery such that their distal ends are spaced away from the abrasive element, and repeating the steps b, c, d, e, and f.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of the embodiments.

The invention claimed is:

1. A method of treating a stenotic lesion in an iliac artery of a patient, the method comprising:
    positioning a rotational atherectomy device in the iliac artery, the rotational atherectomy device comprising:
        a drive shaft that defines a longitudinal axis, the drive shaft being flexible and rotatable, the drive shaft having an elongated proximal portion and an elongated distal portion;
        an abrasive element mounted to the drive shaft between the elongated proximal and distal portions of the drive shaft and configured for rapid rotation together with the drive shaft, the abrasive element having a center of mass that is eccentric from the longitudinal axis of the drive shaft;
        a proximal drive shaft centering element, the proximal drive shaft centering element being coaxially disposed about the elongated proximal portion of the drive shaft and configured to center at least a portion of the elongated proximal portion of the drive shaft during rotation of the drive shaft; and
        a distal drive shaft centering element, the distal drive shaft centering element being coaxially disposed about the elongated distal portion of the drive shaft and configured to center at least a portion of the elongated distal portion of the drive shaft during rotation of the drive shaft, wherein the elongated distal portion extends distally beyond a distal-most end of the distal drive shaft centering element,
    wherein the drive shaft is positioned such that at least the elongated proximal portion extends out of the patient through a first percutaneous access opening to a femoral artery that is ipsilateral to the stenotic lesion in the iliac artery;
    rotating, by a prime mover coupled to the drive shaft, the drive shaft such that the abrasive element follows an orbit because of centrifugal force generated by rotation of the abrasive element; and
    translating, by an advancer mechanism coupled to the drive shaft, the abrasive element back and forth across the stenotic lesion.

2. The method of claim 1, wherein the rotational atherectomy device further comprises a pair of elongate drive shaft sheaths configured for slidably receiving the proximal portion of the drive shaft within one sheath and the distal portion of the drive shaft within the other sheath, the drive shaft sheaths having distal ends and configured for extending around the drive shaft into the treated iliac artery such that the distal ends of the sheaths are positioned in the artery spaced away from the abrasive element, the space between the distal ends of the drive shaft sheaths allowing the rotating abrasive element to move back and forth across stenotic lesion.

3. The method of claim 2, wherein the proximal drive shaft centering element is mounted to the distal end portion or one of the drive shaft sheaths, and wherein the distal drive shaft centering element is mounted to the distal end portion of the other of the drive shaft sheaths.

4. The method of claim 3, wherein the proximal drive shaft centering element and the distal drive shaft centering element are each balloon devices.

5. A method of treating a stenotic lesion in an iliac artery of a patient, the method comprising:
    positioning a rotational atherectomy device in the iliac artery, the rotational atherectomy device comprising:
        a drive shaft that defines a longitudinal axis, the drive shaft being flexible and rotatable, the drive shaft having an elongated proximal portion and an elongated distal portion;
        an eccentric abrasive element mounted to the drive shaft between the elongated proximal and distal portions of the drive shaft and configured for rapid rotation together with the drive shaft, the abrasive element having a center of mass that is eccentric from the longitudinal axis of the drive shaft;
        at least a first elongate drive shaft sheath having a lumen through which the drive shaft extends toward the iliac artery and being configured to remain stationary while the drive shaft rotates; and
        a distal stability element being positioned coaxially with the elongated distal portion of the drive shaft and configured to provide stability to the elongated distal portion of the drive shaft while the drive shaft rotates, wherein the elongated distal portion of the drive shaft extends distally beyond a distal-most end of the distal stability element,
    wherein the drive shaft is positioned such that at least the elongated proximal portion extends out of the patient through a first percutaneous access opening to a femoral artery that is ipsilateral to the stenotic lesion in the iliac artery;

rotating, by a prime mover coupled to the drive shaft, the drive shaft such that the eccentric abrasive element follows an orbit because of centrifugal force generated by rotation of the eccentric abrasive element; and translating, by an advancer mechanism coupled to the drive shaft, the eccentric abrasive element back and forth across the stenotic lesion during the orbit of the eccentric abrasive element.

6. The method of claim 5, wherein the rotational atherectomy device in the iliac artery further comprises a proximal balloon element mounted on a distal end of the first elongate drive shaft sheath and configured to abut with an artery wall so as to provide stability to the elongated proximal portion of the drive shaft while the drive shaft rotates.

7. The method of claim 6, wherein the proximal balloon element comprises an occlusion balloon configured to restrict the flow of fluid around a perimeter of the first elongate drive shaft sheath.

8. The method of claim 5, wherein the distal stability element comprises a distal balloon element mounted on a distal end of a second elongate drive shaft sheath and configured to abut with the artery wall so as to provide stability to the elongated distal portion of the drive shaft while the drive shaft rotates.

9. The method of claim 8, wherein the distal balloon element comprises an occlusion balloon configured to restrict the flow of fluid around a perimeter of the second elongate drive shaft sheath.

10. The method of claim 5, further comprising a source of pressurized fluid for supplying a fluid through the first drive shaft sheath and toward the eccentric abrasive element.

11. The method of claim 5, wherein the elongated distal portion of the drive shaft extends at least 15 cm distally beyond a distal-most end of the distal stability element.

12. The method of claim 5, wherein said positioning a rotational atherectomy device in the iliac artery comprises advancing the drive shaft over a guidewire, the method further comprising withdrawing the guidewire from the drive shaft after advancing the drive shaft over the guidewire.

13. The method of claim 5, wherein the rotational atherectomy device comprises the first elongate drive shaft sheath and a second elongate drive shaft sheath, the first elongate drive shaft sheath being configured for slidably receiving the proximal portion of the drive shaft and the second elongate drive shaft sheath being configured for slidably receiving the distal portion of the drive shaft within the other sheath, the first and second drive shaft sheaths having distal ends and configured for extending around the drive shaft into the treated iliac artery such that the distal ends of the sheaths are positioned in the artery spaced away from the eccentric abrasive element, the space between the distal ends of the drive shaft sheaths allowing the rotating abrasive element to move back and forth across stenotic lesion.

14. The method of claim 13, further comprising a source of pressurized fluid for supplying a fluid through the first drive shaft sheath and aspirating the fluid and abraded particles through the second drive shaft sheath.

15. The method of claim 5, wherein a second percutaneous access opening is located in a femoral artery which is contralateral with respect to the iliac artery, and wherein the elongated distal portion of the distal drive shaft extends out of the patient through the second percutaneous access opening.

16. The method of claim 5, wherein a second percutaneous access opening is located in an artery of the upper extremity of the patient, and wherein the elongated distal portion of the distal drive shaft extends out of the patient through the second percutaneous access opening.

17. The method of claim 5, wherein during the rotating of the drive shaft the distal stability element causes at least a portion of the elongated distal portion of the drive shaft to be positioned generally centrally within the iliac artery.

18. The method of claim 5, wherein the drive shaft is configured to extend throughout an entire length of the iliac artery.

* * * * *